United States Patent [19]
Teare et al.

[11] Patent Number: 5,467,656
[45] Date of Patent: Nov. 21, 1995

[54] MEASUREMENT SYSTEM FOR HAND TOOLS

[75] Inventors: Peter R. Teare, Westborough; Patrice L. Murphy, Mendon; George E. Brogmus, Hopkinton, all of Mass.

[73] Assignee: Liberty Mutual Insurance Co., Boston, Mass.

[21] Appl. No.: 139,546

[22] Filed: Oct. 20, 1993

[51] Int. Cl.$^6$ ........................................ G01L 1/00
[52] U.S. Cl. .................. 73/862.541; 73/379.02; 273/81 R
[58] Field of Search ............ 73/379.02, 379.03, 73/862.541; 128/774; 273/29 A, 75, 81 R, 166, 187.5; 482/49; 364/413.02, 413.04

[56] References Cited

U.S. PATENT DOCUMENTS

| | | | |
|---|---|---|---|
| 4,231,255 | 11/1980 | Haski et al. | 73/379 |
| 4,337,050 | 6/1982 | Engalitcheff, Jr. | 434/260 |
| 4,558,864 | 12/1985 | Medwedeff | 482/49 X |
| 4,774,966 | 10/1988 | Lemmen | 128/774 |
| 4,824,103 | 4/1989 | Smidt | 73/379.02 X |
| 4,885,687 | 12/1989 | Carey | 364/413.2 |
| 4,949,729 | 8/1990 | Haski | 128/774 |
| 4,953,862 | 9/1990 | Uke et al. | 273/81 R X |
| 5,088,734 | 2/1992 | Glava | 273/81 R X |
| 5,125,270 | 6/1992 | Kovacevic | 73/379 |
| 5,174,154 | 12/1992 | Edwards | 73/379 |
| 5,186,695 | 2/1993 | Mangseth et al. | 364/413.02 X |

OTHER PUBLICATIONS

Kadefors, et al., "Ergonomic Evaluation of Hand Tools: A Case Study On Plate Shears," 1993.
Wyvill et al., "Ergonomics Update: An Overview of Research Activities to Develop an Ergonomic Work Assesment System At Georgia Tech." 1993.

Primary Examiner—Richard Chilcot
Assistant Examiner—Elizabeth L. Dougherty
Attorney, Agent, or Firm—Wolf, Greenfield & Sacks

[57] ABSTRACT

A measurement system for measuring hand tools includes a number of instrumented tools and a data collector. The data collector has a processor which can operate in a task analysis mode in which data is received, stored, and processed over a user-determined period of time. A number of different tools with different adaptor configurations can be coupled to a receptacle on the housing of the data collector. The collector has recognition circuitry for determining which type of tool is plugged into the receptacle, and, in response, the processor retrieves parameters needed to process the data and which are related to the recognized tool. The instrumented tools are designed to simulate actual tools used in the work place, and thus have substantially the same size, shape, weight, weight distribution, and feel of actual working models of the tools. The sensors can include strain gages for measuring force and torque, position detectors for measuring hand position, sensors for measuring grip, accelerometers for measuring acceleration of the tools and sensors for measuring an angle of rotation of a tool.

54 Claims, 7 Drawing Sheets

MEASUREMENT SYSTEM FOR HAND TOOLS

FIELD OF THE INVENTION

This invention relates to a system for measuring forces exerted by a hand tool when it is used by a worker.

BACKGROUND OF THE INVENTION

Many occupations require repetitive hand motion and/or repetitive use of hand tools, such as pliers, knives, screwdrivers, and cutting snips. Recently, there has been significant attention to, and increased reporting of, cumulative trauma disorders (CTD's) which may be related to such repetitive hand motion. One CTD, for example, is carpal tunnel syndrome. This syndrome includes swelling of the median nerve, or thickening of the carpal ligament in the hand. The physiology of this syndrome is described in more detail in U.S. Pat. No. 4,774,966.

Diagnostic devices have been developed for testing forces exerted by the hand. These devices include, for example, a carpal tunnel syndrome screening device, U.S. Pat. No. 4,774,966; a grip rate measurement, U.S. Pat. No. 4,949,729; and a human hand load sensor, U.S. Pat. No. 5,125,270. The devices in these patents are specially designed test pieces of equipment for measuring forces by the hand of a person. Since these pieces of equipment are not similar to workplace tools, the tests do not provide data which reflects conditions which are encountered by a worker in a working environment. These devices typically test controlled individual movements over a short period of time, but do not provide information regarding extended repetitive use which is more typical of the workplace.

SUMMARY OF THE INVENTION

According to the present invention, a measurement system measures forces exerted by a tool, and, may additionally measure positions of a worker's hand when a hand tool is used, acceleration of the hand or tool, and angular movement of the tool. These measurements can be used to detect force characteristics of tools and tasks that may have a high risk associated with cumulative trauma injuries, to instruct workers on preferred methods for using the tools, to detect forces for rehabilitation of an injured worker, to redesign the tool, and/or to redesign the task for which the tool is used.

The hand tools are instrumented to provide force-related information which is relevant to the individual tool. Preferably, the instrumented tools have substantially the same weight, weight distribution, size, shape, surface texture, and feel of a non-instrumented tool which is normally used by a worker in the work environment. A number of different types of instrumented tools can be employed, such as a pair of pliers, a boning knife, a screwdriver, textile snips, and a wrench. The tools each have one or more sensors which detect force, torque, acceleration, linear position, and/or angular position. These sensors may include foil strain gages, accelerometers, linear displacement transducers, and potentiometers. (The term "force" is used herein not only to refer strictly to the product of mass and acceleration, but also may collectively refer to other force-related measurements, including torque and acceleration.)

A data collector is coupled to a tool to collect, process, and display data. The sensors in the tools provide analog voltage signals through an adapter which has pins. These pins mate with openings in a receptacle which is preferably mounted on the data collector housing. For each type of tool, preferably a group of pins provide an identification code which is unique to the type of tool. The identification code may be based on selectively short-ciruiting and open-circuiting certain pins reserved for identification purposes. The data collector has a processor which recognizes the type of tool from the identification code and accesses a stored program to determine parameters that are used for data processing and display. The parameters include conversion numbers for converting an input signal from a sensor to an output in selected units of measurement, such as units of force or acceleration. Where there are multiple sensors, the data collector may convert some signals to one type of units, and other signals to other units. The data collector periodically checks to determine whether the tool has been replaced with another type of tool.

The data collector can collect and display data in a number of different modes, including a real time mode, an average mode, and a task analysis mode. In the task analysis mode, the processor collects data, stores it in memory for a desired collection time, and post-processes the stored data. The stored data can also be downloaded to another computer for long term storage and further analysis. A user can thus compare data collected at one time with data collected at another. This ability to compare data collected at different times is useful, for example, to compare tools or tasks when changes are made.

As part of the post-processing, the data collector determines how many repetitions were made and when they were made with the tool during the time that data is collected and stored. To determine the number of repetitions, the processor uses rules which are specific to each type of tool, the rules being determined in response to the identification code. The rules include threshold parameters, such as the magnitude of the change in force versus time, to determine when a repetition has occurred. The processor calculates information to be displayed from the stored data including number of repetitions; average and peak force for each repetition and for the selected time period; and the duration of forceful exertion for each repetition and for all repetitions.

Other detectors can also be employed on the tool or on the hand of a worker. A position detector may be positioned on the hand for detecting hand or wrist position while using the tool, or it can be incorporated on the tool itself. Some tools, such as a knife, may be instrumented with an accelerometer on the handle for measuring the acceleration as the tool is used. The accelerometer can, for example, be mounted on a handle of the tool. Tools may be equipped to provide a measure of angular rotation. In the case of the pliers, for example, a potentiometer may be coupled to the fulcrum to indicate the relative position of the plier handles during forceful exertions.

Each of these detectors—position, accelerometer, or angular position—can provide a signal which is synchronized with the force-related signals. By observing the synchronized signals, a user can determine relationships between the forces exerted by the tool and the position, acceleration, and/or angular position. This information can be useful in redesigning tools and/or tasks to reduce the forces exerted by the tool.

According to the present invention, the measurement system allows a user to measure a force exerted by a tool in a worker's hand in the worker's actual working environment. The instrumented tools have substantially the same weight, weight distribution, feel, size, shape, and surface texture of a tool which is actually used in the work place.

Consequently, the measurements accurately reflect forces in a work environment without requiring the worker to perform movements which would otherwise be needed to compensate for variations between an instrumented tool and an actual tool.

BRIEF DESCRIPTION OF THE DRAWINGS

Other features and advantages will become apparent from the following detailed description when read in conjunction with the following figures in which.

DETAILED DESCRIPTION

According to the present invention, a measurement system is provided for measuring forces exerted by a hand tool when the hand tool is used by a worker. The tools are instrumented so that they simulate tools which are used by workers in actual practice. The system can measure force, torque, acceleration, position, and/or angular rotation of the tool, and position and/or acceleration of the hand. A data collector can process and display interpreted results conveniently for a user.

Figure 1:
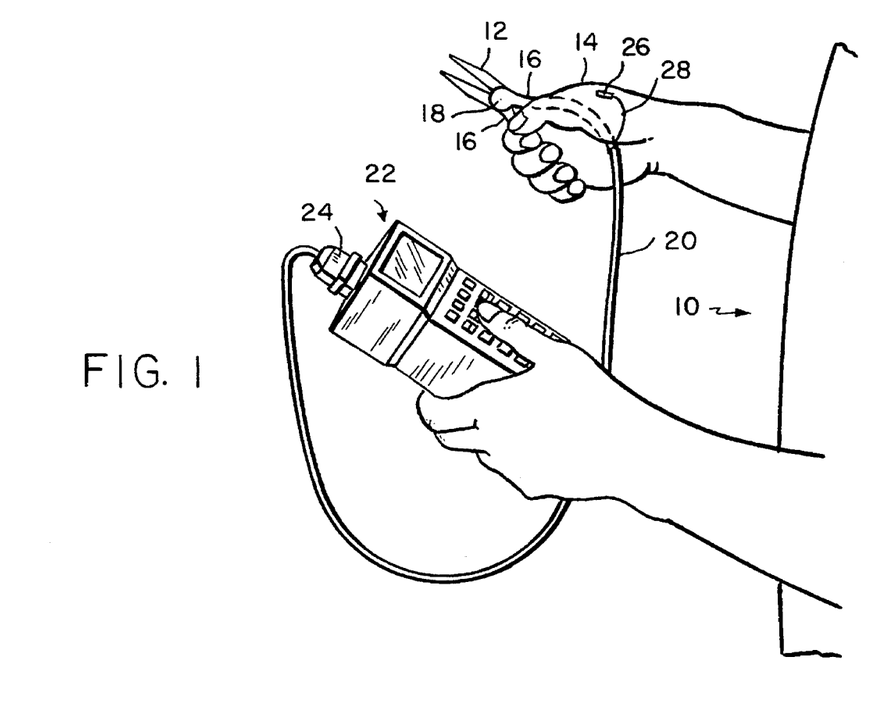
FIG. 1 is a perspective view of an instrumented tool and a data collector according to the present invention.
Figure 2A:
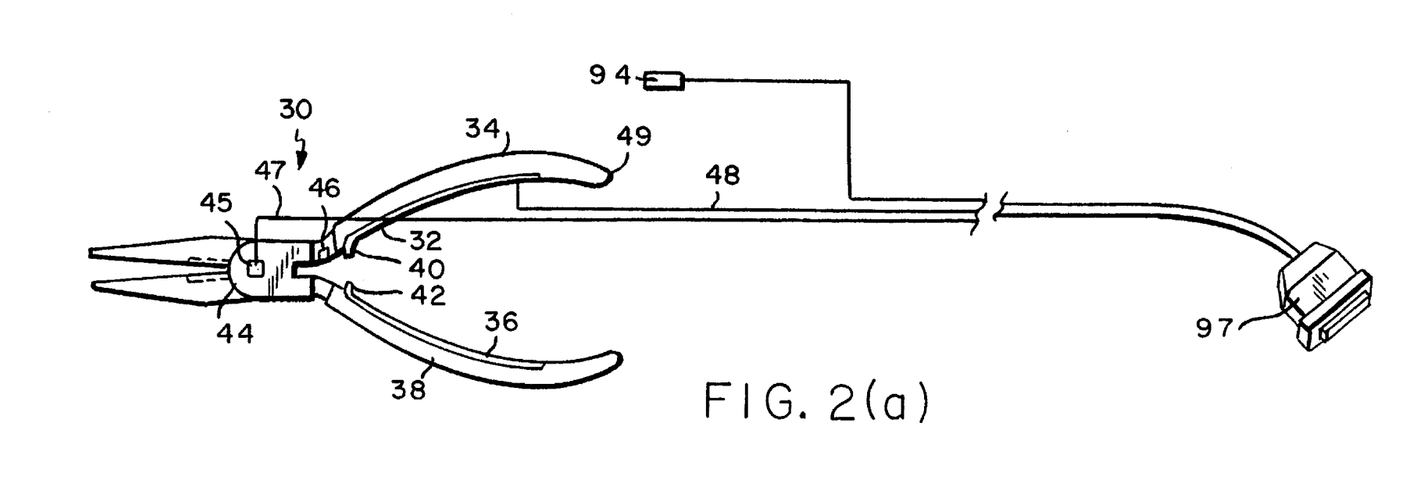
FIGS. 2(a)–2(c) are perspectives view of a number of instrumented tools according to the present invention.

Referring to FIG. 1, a person 10 holds an instrumented tool 12 in hand 14. Tool 12 is a pair of pliers which has two handles 16 which are pivotally connected around fulcrum 18. Sensors 46, 49 (FIG. 2) are provided on the tool to measure torque exerted by hand 14 when handles 16 are compressed, and an angle of movement of the pliers, respectively. The sensors provide analog voltage signals over cable 20 to data collector 22. The data collector is coupled to cable 20 through an adapter 24.

A position sensor 26 is mounted on hand 14 and provides a position signal over cable 28. Cable 28 can be combined with cable 20 to provide the position signal synchronized with the other signals from sensors 46, 49. (In this description, "cable" typically refers to a number of wires.) The position sensor is typically a linear voltage transducer or potentiometer which is first zeroed in an anatomically neutral position. The transducer then provides a signal indicating change in position.

Figure 2B:
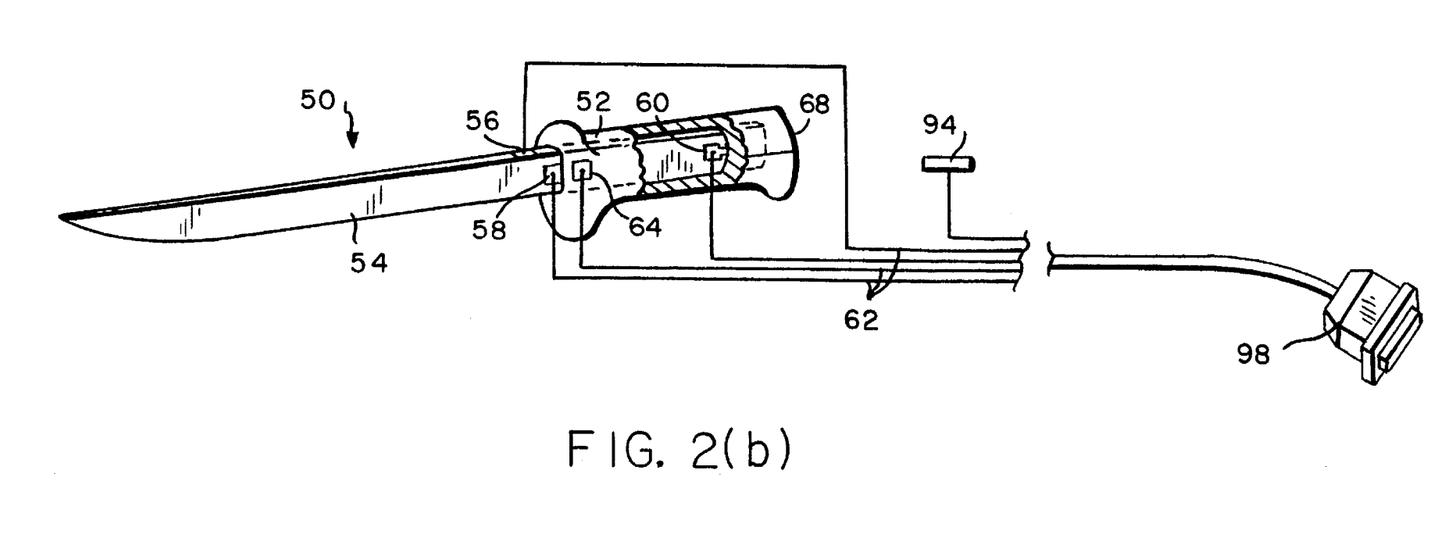
Figure 2C:
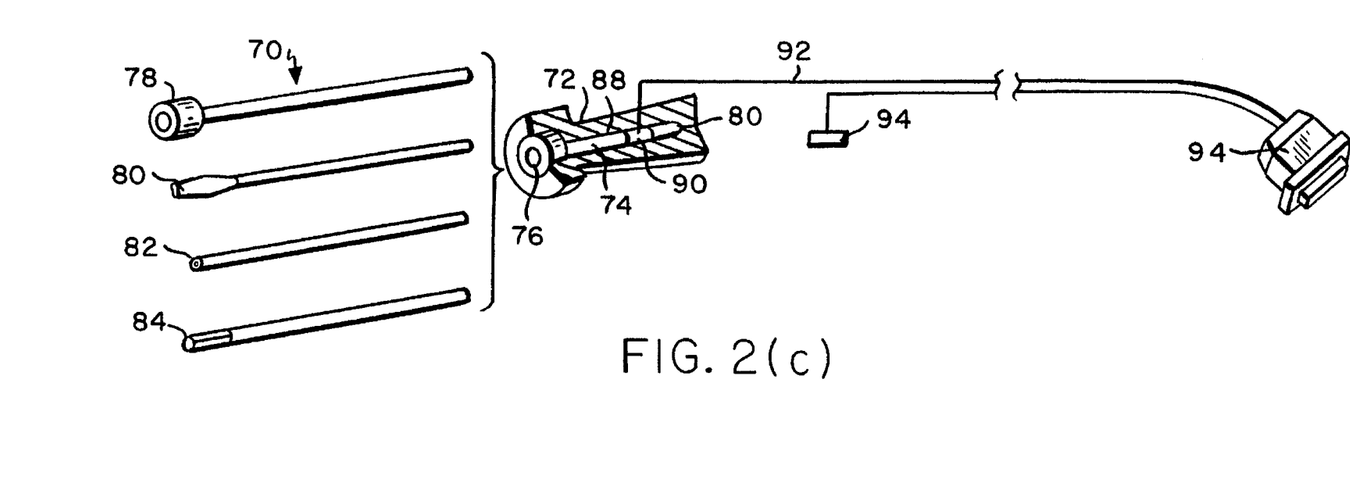

Referring to FIGS. 2(a)–2(c), a number of different instrumented work tools can be employed for measurement. Each of these tools is a version of an actual tool which has been instrumented to have one or more sensors for providing signals indicating force, torque, acceleration, position, and/ or angular movement. The types of sensors which are used will vary depending on which measurements are relevant for the particular type of tool. Other types of tools, such as wrenches or textile snips, could also be similarly instrumented. Preferably, the instrumented versions of the tools have substantially the same weight, weight distribution, feel, surface texture, size, and shape as a tool which is used in the workplace. Such instrumentation allows a user to get the best possible field measurement, since the worker does not perform compensatory movements for differences between the instrumented tool and the workplace tool. A pair of pliers 30, shown in FIG. 2(a), has two handles 34, 38 which are brought together and rotate about a fulcrum. A sensor 46 has two foil strain gages mounted on each side of handle 34. The strain gages are incorporated in a full Wheatstone bridge circuit (not shown). Sensor 46 thus provides an analog voltage signal over cable 48 representative of the total torque about the fulcrum. An angle sensing potentiometer 45 is positioned at fulcrum 44 for measuring the relative rotation of the handles at the fulcrum. The potentiometer provides over a cable 49 an analog voltage signal which is related to the angular position. Cables 47, 48 each pass through a channel (not shown) in the handle so that they do not interfere with the worker using the pliers. While the cables are shown schematically in FIG. 2(a) for simplicity, it should be understood that they are preferably channelled in the pliers so that they appear, on visual inspection, only to enter handle 34 at an end 49. In one embodiment of a pair of pliers, metal springs 32, 36 are located on the inside of handles 34, 38. These springs each have a curved end portion 40, 42 near a fulcrum 44 which is compresses when the handles are brought together. With such springs, the sensor should be between the springs and the fulcrum. Other tools which operate in a similar manner, such as a textile snip or cutting shears, could be similarly instrumented.

A boning knife 50, shown in FIG. 2(b), has a handle 52 and a blade 54. Sensors 56, 58 are mounted on the handle 54 to measure the deflection of the handle in two orthogonal directions. Sensor 58 detects positive and negative bending in the direction of cutting, while sensor 56 measures bending which is transverse to the cutting direction. Each sensor 56, 58 has four strain gages which are wired into a full Wheatstone bridge circuit (not shown), and four wires for providing signals. A grip sensor 60 includes a foil strain gage which is mounted in the handle to detect force of the grip exerted by the handle when the tool is used by a worker. An accelerometer 64 is also coupled to the handle and provides a signal. Signals from all of these sensors are provided over cables which are collectively indicated as 62. The cables are preferably channeled through the knife handle and extend out of the base 68 of the handle so that the cables are not visible except at the base and do not interfere with a worker's operation of the knife.

The grip sensor could, alternatively be mounted on the exterior of the handle and could include a force sensitive resistor, or ultrasound force measurement sheets.

A multi-tool assembly 70, shown in FIG. 2(c), has a handle 72 which has an adapter 74 mounted longitudinally in the center of the handle. At the end of adapter 74 is a receptacle 76 to which a number of different attachments, such as nut driver 78, screwdriver 80, phillips head 82, and allen spline 84, can be removably coupled. Adapter 74 is rigidly coupled to the handle at one end 86, while over most of the length of the adapter, there is a small space 88 between handle 72 and adapter 74. Sensor 90 has foil strain gages which are incorporated in a full Wheatstone bridge circuit (not shown), and which are mounted on the adapter. Since adapter 74 is only rigidly coupled at one end, when a user rotates the handle to operate the nutdriver or screwdriver, a rotational deflection can be detected between adapter 74 and handle 72. A voltage signal proportional to the deflection is provided over cable 92. Attachments 78–84 are removable to allow more flexibility. Alternatively, an instrumented tool, such as a screwdriver, could be made without removable attachments.

A position sensor 94 also can be provided with each tool. By processing this signal, a velocity or acceleration can be determined by taking derivatives. For more accurate measurements, however, it is preferable to use an accelerometer which is typically mounted on the tool or on the hand for determining acceleration. Grip sensors can be provided in other tools when appropriate. For sensors with a Wheatstone bridge, a 5 volt regulated supply is provided from the data collector.

Figure 2D:
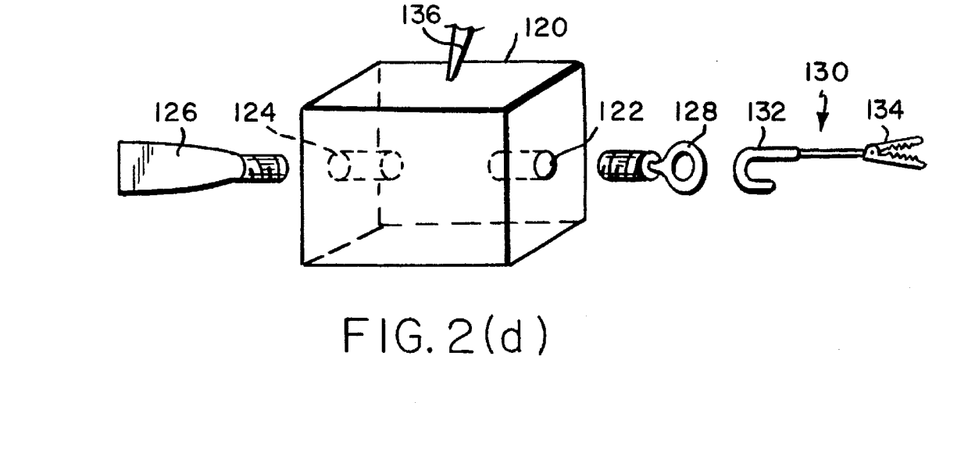
FIGS. 2(d)–2(e) are perspective views of other test devices which may be used for measuring forces.
Figure 2E:
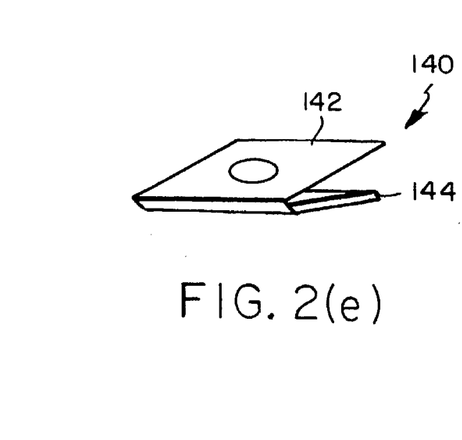

Other devices, shown in FIGS. 2(d)–2(e), can be used to measure force exerted on a tool, and can be packaged in a measurement kit with the instrumented tools shown in FIGS. 2(a)–2(c). Referring to FIG. 2(d), a generally box-shaped force transducer 120 has two threaded openings 122, 124 on opposite faces. These openings receive attachments such as a handle 126 at one end and a loop 128 at the other. Loop 128 can be connected on one of a number of further attachments, such as an alligator clip assembly 130 which has a hook 132 at one end for engaging the loop and a springed, toothed end 134 for clamping an object. Depending on the measurement need, a different attachment can be provided, such as other clamps, hooks, or straps. The transducer can be used to measure force exerted by other devices, such as handles, levers, knobs, or dials which must be used by workers. The transducer provides a signal over cable 136. Such transducers are available, for example, from HBM, Inc. of Marlboro, Mass.

Referring to FIG. 2(e), a pinch gage 140 is a dynamometer which has two plates 142, 144 which are connected with a spring (not shown). The pinch gage and the transducer in FIG. 2(d) may each be a stand-alone devices which include their own visible output mechanism (not shown) for receiving the signals and for providing an indication of the force exerted by the gage. A larger or differently configured pinch gage can also be used to measure hand grip.

A pinch gage can be used as a substitute for specific tools which have not been instrumented, or can be used for comparative tests with instrumented tools. A worker can be instructed to use the pinch gage to apply a similar force to the force which is normally applied by the worker in a work activity. Thus, simulated results can be obtained. If instrumented tools are available, it may also be useful to compare the estimated force of operation with the actual force determined by the instrumented tool.

Figure 4:
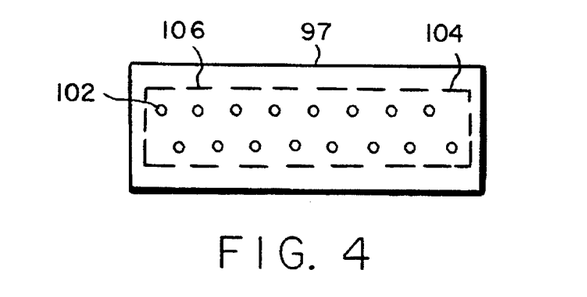
FIG. 4 is an end view of an adapter.

Referring again to FIGS. 2(a)–2(c), pliers 30, knife 50, and multi-tool assembly 70 have adapters 97, 98, and 99, respectively, for coupling the signals from the sensors to a series of pins. Referring also to FIG. 4, the adapters are very similar to each other in size and outward appearance, and each has sixteen pins 102. The pins are different, however, depending on the tool. A group 104 of four pins in each adapter are reserved to provide a digital identification code, and thus up to sixteen different types of tools can be identified. The code is determined by selectively short-circuiting and open-circuiting pins. The pins are coupled to pins (not shown) of a processor (FIG. 5) when the adapter is plugged into a mating receptacle on the data collector. Thus a high or low voltage at each of the four processor pins indicates the code, and thus the type of tool. The remaining twelve pins of the adapter are connected to the various sensors to provide analog data to data collector 22. Some pins may be used to provide a voltage signal to the sensor-, such as a regulated five volt supply voltage for the strain gages in the Wheatstone bridge.

In other embodiments, the number of pins and their allocation between data collection from sensors and identification data could be varied as needed. Thus one could collect more data by expanding the data pins, and increase or decrease the number of different types of tools.

Figure 3:
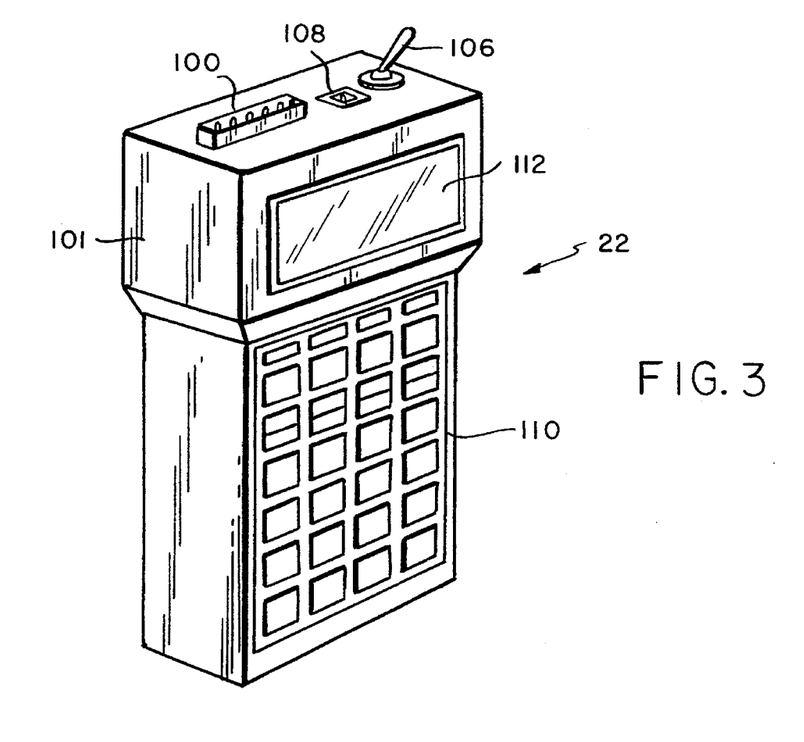
FIG. 3 is a perspective view of the data collector.

Referring to FIG. 3, data collector 22 has a receptacle 100 mounted on the housing 101 for receiving and mating with an adapter. A user interface on the data collector includes a keypad 110 and a liquid crystal display 112. The keypad, which is environmentally sealed, allows the user to enter data or to select a mode of operation for the data collector. The liquid crystal display provides easily readable data to a user. Data collector 22 is light-weight, portable, and hand-held, and is preferably powered with rechargeable batteries. In an exemplary embodiment, the data collector weighs less than two pounds, and measures 7.5×3.5×1.5 (in inches). Switch 106 is an on/off switch. Input port 108 includes a terminal for recharging the battery, and a terminal for downloading stored data to, and for uploading programming data from an external computer (not shown).

Figure 5:
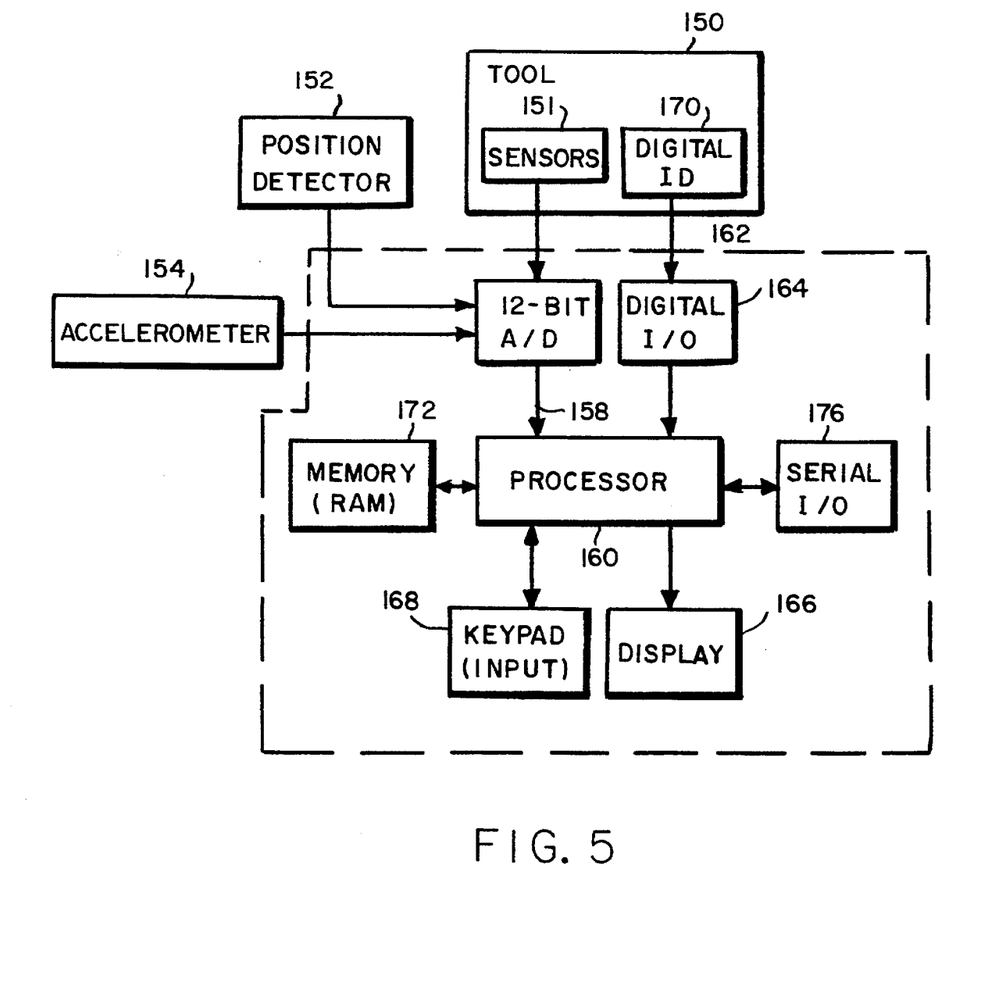
FIG. 5 is a block diagram of the control system of the data collector according to the present invention.
Figure 6:
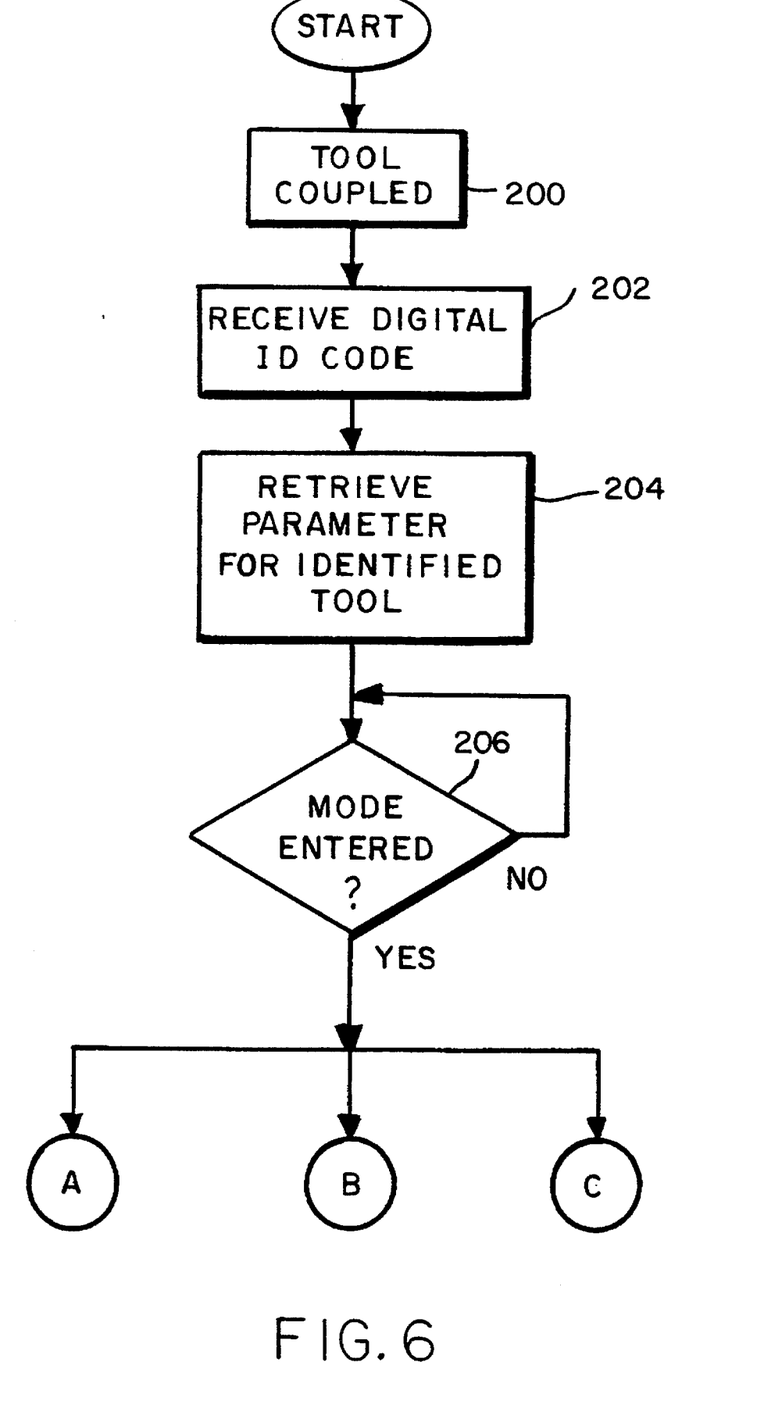
FIGS. 6–10 are flow charts of operation of the data collector according to the present invention.

A block diagram of the circuitry and control system of the data collector of the present invention is shown in FIG. 5. Sensors 151 on an instrumented tool 150, a position detector 152, and an accelerometer 154 provide analog data to data collector 156. The data collector has a 12-bit analog-to-digital converter 156 which receives the analog data and provides digital data 158 to a processor 160.

Tool 150 also provides digital identification data 162 via the pin configuration of the adapter through a digital I/O 164 to the processor. The processor receives identification data from tool 150, digital data 158 from converter 156, and user inputs from keypad 168, performs calculations, and provides output signals to a liquid crystal display 166. The form of the data which is presented to the user is determined by the user through inputs on keypad 168. A serial I/O interface 176 allows a user to download stored data from the memory to a computer, or to reprogram the processor when new tools or analytical functions are added.

Different instrumented tools have different requirements for performing calculations and presenting data. Some tools, such as the pliers, measure one force (compression) in one direction. Other tools, however, such as the knife, may measure two or more different forces, each of which may be in more than one direction (and thus defined as positive and negative). Consequently, calibration factors and units will be different, depending on the type of tool used.

When a tool is coupled to the data collector, the digital identification 170 received by processor 160 through the pin arrangement of the adapter causes the processor to access a program which is written into the processor. The program includes various parameters for each type of tool. The processor thus can retrieve the appropriate parameters relating to the particular type of tool. The processor causes the name of the tool to be indicated on the display. Periodically, the processor checks to determine whether a new tool has been coupled to the data collector.

These parameters include slope thresholds for determining repetitions (discussed below) and parameters for converting the input signals from the sensors to meaningful output signals. Analog data, typically received in millivolts, is converted to digital data 158 and can be represented numerically as counts in a predetermined range. The counts are a non-calibrated magnitude of the input signal over time. For each tool, a conversion factor in terms of counts/unit indicates a relationship between counts and the characteristic detected by the sensor, such as force-related units, such as pounds or foot-pounds, degrees of angular rotation, or units of position.

Flow charts in FIGS. 6–9 illustrate the processes used by the processor in response to user-selected modes of operation. As described above, when the tool is coupled to the data collector (step 200), the processor determines the type of tool from the digital identification (step 202), and retrieves appropriate parameters (step 204) for the particular type of tool from the stored program. The processor next determines whether a user has entered a particular mode of operation (step 206).

Figure 7:
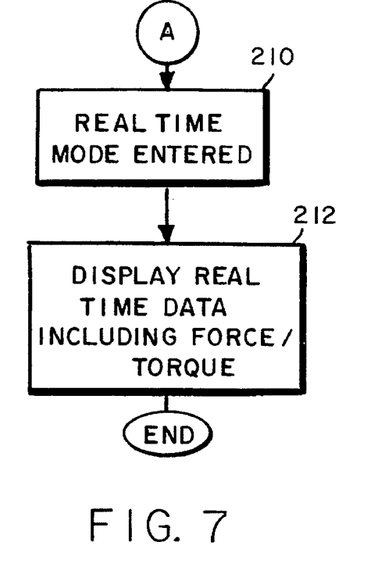
Figure 8:
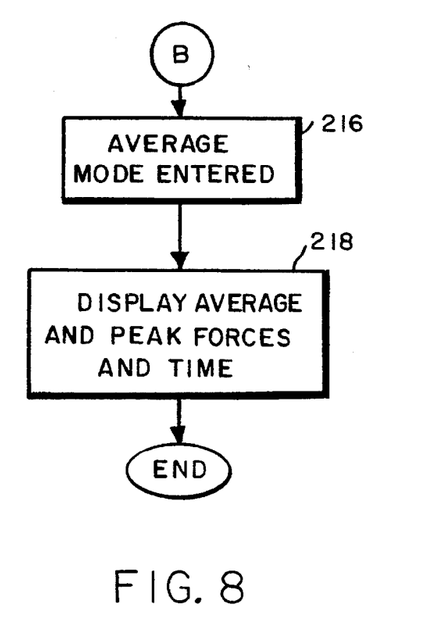

Referring to FIG. 7, if a real time mode is entered (step 210), the processor causes the display to indicate real time data such as real time force, peak force, angular position, and the time (step 212). Referring to FIG. 8, if average mode is entered (step 216), the processor directs the display to show averaged values, such as average force and peak force (step 218) over the time that the force is measured. The time can be either from the start time or from a later time which is designated as the beginning time for averaging purposes.

Figure 9:
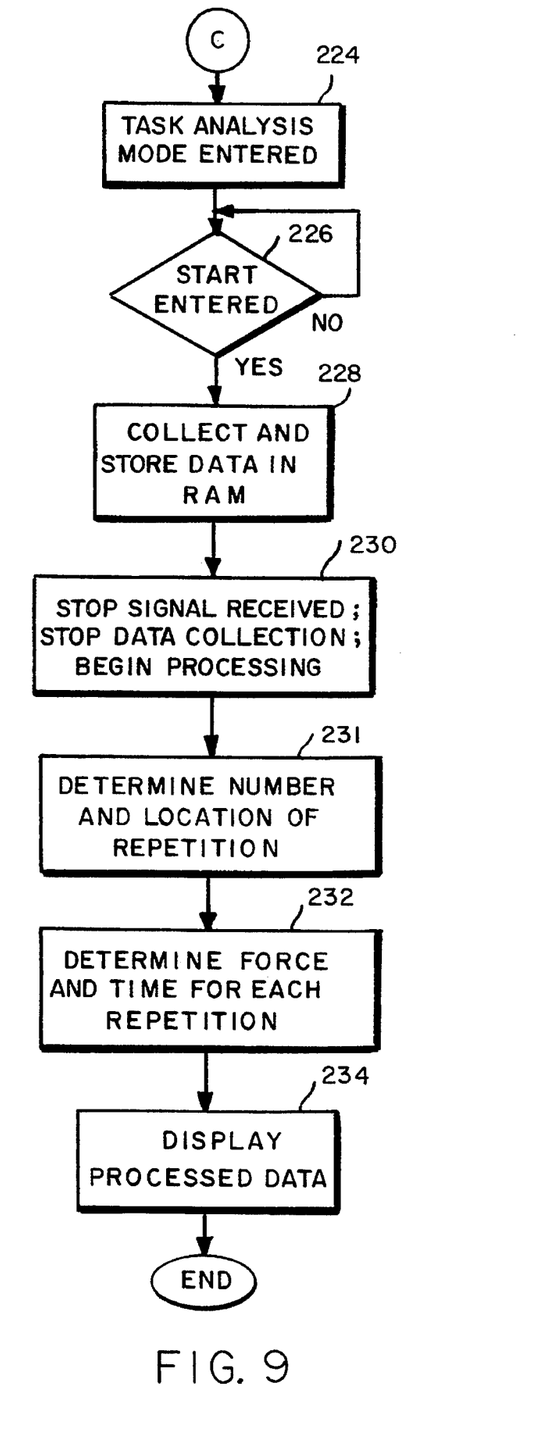

Referring to FIG. 9, if task analysis mode is selected and entered by the user (step 224), the processor prompts the user to indicate when to begin data collection, and waits until the user indicates when to start by pressing a start key (not shown) on the keypad (step 226). The user allows a worker to operate the instrumented tool as he or she would in a normal working environment over a normal number of repetitions with the tool, e.g., a number of compressions with the pliers or a number of cuts with the knife. The processor collects and stores the digitized data in memory (step 228) until the user indicates that the processor should stop storing data by pressing a stop key (not shown) on the keypad. A stop signal is received by the processor (step 230), and the processor begins post-processing the stored data. If a maximum time for data collection is exceeded, the data collector can stop data collection or can overwrite the data previously stored in memory starting at the first data set stored, or a signal can be provided to the user indicating the end of available storage.

The processor determines the number of repetitions which have occurred by analyzing the signal after the signal has been stored (step 231). Different techniques may be used for determining repetitions, depending on the type of tool which is used. The appropriate technique is known to the processor when the threshold parameters are accessed in the stored program in response to the identification signal for the type of tool.

Figure 11:
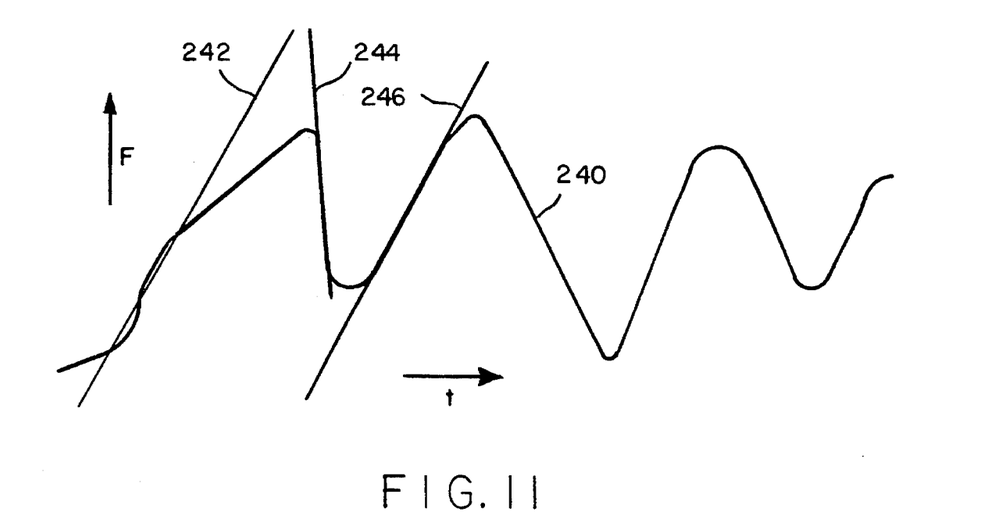
FIG. 11 is a graph illustrating a signal and slope thresholds.

An example of the determination of repetitions is illustrated in connection with FIG. 11. If the tool being used is a pair of pliers, for example, the processor checks signal 240 (which indicates a force versus time from the strain gage) for an upward slope 242 having a magnitude exceeding a predetermined threshold slope, followed by a downward slope 244 having a magnitude exceeding a predetermined threshold slope, followed by another upward slope 246 having a magnitude exceeding a predetermined threshold slope. When these slopes are detected, the processor determines that a positive repetition has occurred between the first upward slope and the first downward slope. The determination may also be based on a minimum time period over which the slope is calculated and/or a minimum threshold for the magnitude of the force. Since the processed data is digital, the time may be expressed as number of samples, where each unit represents the sample time of the analog-to-digital converter.

The sensor in a pair of pliers has only positive repetitions because the sensor only detects compression. In input signals from sensors in other tools, such as the knife, the forces may be in two directions, so positive and negative repetitions are determined. In addition to detecting a positive repetition which has a pattern of slopes which are upward, downward, and upward, the processor may additionally detect sequences of slopes which are downward, upward, and downward, thus indicating a negative repetition.

For different types of tools, the rules may be different, or may involve different types of repetitions. In the case of the knife, for example, a number of positive and negative repetitions may be determined separately for the sensor which measures force in the cutting direction, and for the sensor which measures force transverse to the cutting direction. Thus the processor determines four different numbers of repetitions, and these four numbers of repetitions may be different from each other. Another possibility for determining repetitions is to have rules used in combination, e.g., one signal must vary by one threshold, while another signal must vary by another threshold.

After determining the location and number of repetitions in the input signals, the processor provides calculated data, such as average force, peak force, and time, for each repetition and for the overall sample time, on the display (step 234). In one preferred embodiment, the processor automatically causes the display to show the number of repetitions, the frequency of repetitions, the duration of each repetition, the aggregate duration of all forceful exertions, and the overall time on an initial screen display. By pressing a key, a user can then access other data relating to average force, average peak force, and maximum peak force for the repetitions. These readings may be obtained both for positive and negative repetitions, and for each of a number of sensors.

Figure 10:
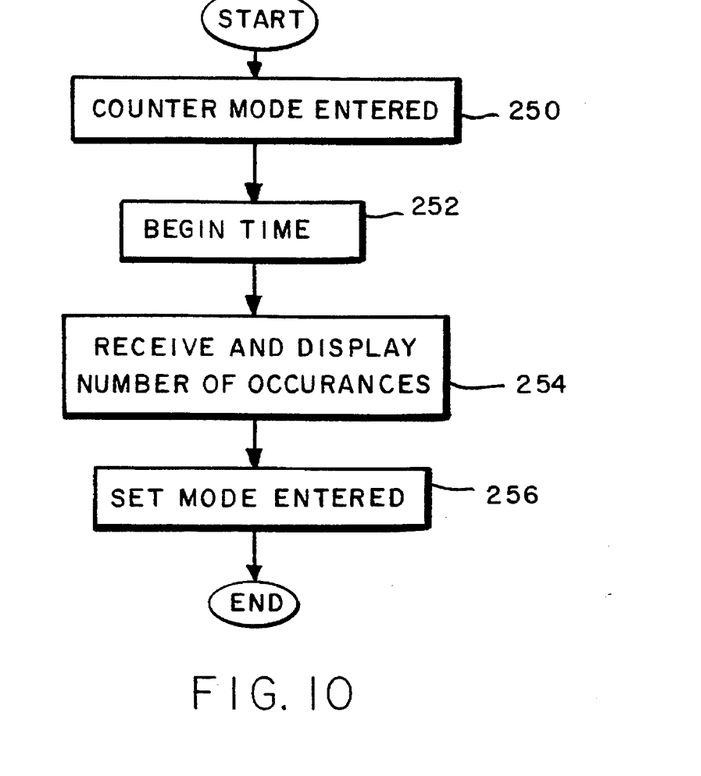

FIG. 10 is a flowchart illustrating another mode of operation of the present invention in which a user selects a counter mode rather than a tool mode (step 250). When this mode is selected, the data collector serves as a counter which displays a number of user-entered occurrences, a time, and a frequency of occurrences. First, the data collecting time begins when a key on the data collector is entered (step 252). A user observes a worker doing a certain repetitive task and presses a key each time the user observes the worker doing one task, and another key when the user observes another task. The data collector receives the data, displays the time and number of occurrences in real time, and provides the frequency of occurrences on the display to the user (step 254). This feature is employed without a tool coupled to the data collector. When set mode is received (step 256), the data collector returns to its original mode.

By using the task analysis mode, a user can collect and process data for a worker in the actual working environment with a tool which simulates as close as possible the weight and feel of a tool actually used. These measurements enable testing of different tools for the least amount of harmful exerted force and number of repetitions, and allow testing of workers for potential health risks. Furthermore, a user can use this information to help determine whether it would be beneficial to redesign the tool, redesign the task, or improve workplace layout.

Having described an embodiment of the present invention, it should be apparent that other variations and modifications may be made to the present invention without departing from the scope of the invention as defined by the appended claims.

For example, in another embodiment, a handle with strain gages could be mounted in parallel to a handle of a tool. The parallel handle could be used to measure torques due to tasks such as painting with a brush or applying spackle. A strain gage would be coupled to the handle. This allows the instrumented tool to serve as a flexible multi-tool attachment. It would be difficult, however, to precisely simulate the weight and weight distribution with a parallel handle.

What is claimed:

1. A system comprising:
    a plurality of different types of hand tools, a tool of each different type including:
        a sensor for detecting a force exerted by the corresponding tool; and
        an adapter electrically coupled to the sensor for providing a signal derived from the detected force; and
    a data collector including:
        a receptacle for removably coupling to the adapters corresponding to the different types of tools,
        means for automatically determining which type of tool is coupled to the receptacle based at least in part on the adapter,
        memory for storing data, the data including parameters corresponding to each different type of tool, and
        means, responsive to the determining means, for accessing the parameters corresponding to the tool which is coupled to the data collector.

2. The system of claim 1 wherein one of each adapter and the receptacle has a plurality of pins and the other of each adapter and the receptacle has a plurality of openings for receiving the pins, the pins being configurable in different arrangements so that each different arrangement corresponds to a different type of tool.

3. The system of claim 1 wherein the data collector further comprises a display coupled to the processor for displaying force data to a user, the force data being derived from the input signals.

4. The system of claim 3 wherein the parameters include conversion factors for converting the input signal from the sensor to an output signal, wherein the conversion factors are separately defined for each tool so that an input signal from a first sensor having a magnitude, and an input signal from a second sensor of another type of tool having the same magnitude result in different output signals.

5. The system of claim 1 wherein the data collector has a hand-held housing for holding the determining means, the memory, and the accessing means.

6. The system of claim 1 wherein the data collector further includes means responsive to the force signal for storing data and for post-processing the stored data to determine when and how many a forceful exertions repetition occurs.

7. An apparatus comprising:
    a hand tool having a first sensor for detecting a first force exerted by the tool when the tool is used by a user and for providing a force signal that is derived at least in part from the detected first force; and
    a processor for receiving the force signal from the tool over a period of time, and for determining when each repetition occurs during the period of time based on the received force signal, wherein the processor determines when each repetition occurs based at least in part on a magnitude or slope of the force signal.

8. The apparatus of claim 7 wherein the processor compares the slope of the force signal to a predetermined slope threshold.

9. The apparatus of claim 8 further comprising a second tool of a type different from the type of the first tool, the second tool having a sensor for detecting force exerted by the tool, the first and second tools having respective first and second adapters for receiving force signals, wherein the processor is electrically coupled to a receptacle for removable and reinsertable coupling with the adapters, the processor having means for recognizing which tool is coupled to the receptacle, and wherein the predetermined slope threshold is based at least in part by the type of tool that is recognized.

10. The apparatus of claim 9 wherein the predetermined slope threshold is based at least in part by the type of tool that is recognized.

11. The apparatus of claim 7 wherein the tool has a second sensor for detecting a second force exerted by the tool, the second force being different from the first force, and wherein the processor receives the first and second force signals.

12. The apparatus of claim 11 wherein the processor has means for determining a first number of repetitions for the first sensor and a second number of repetitions for the second sensor, the first number and the second number being determined independently.

13. The apparatus of claim 12 wherein the processor determines positive and negative repetitions for each sensor.

14. The apparatus of claim 7 wherein the processor determines a duration for each repetition.

15. The apparatus of claim 7 wherein the data collector further comprises a memory for storing the received force signal, the processor determining that a repetition has occurred after the data has been stored.

16. The apparatus of claim 7 wherein the hand tool is universally movable by a user for the period of time and wherein the processor accumulates a number of repetitions during the period of time.

17. The apparatus of claim 7 further including a hand-held housing for holding the processor.

18. An apparatus comprising:
    a hand tool having a sensor for detecting a force exerted by the tool when a user operates the tool and for providing a force signal;
    a position detector coupled to the user's hand for detecting the position of the hand as the hand operates the tool and for providing a position signal;
    a data collector coupled to the tool and to the position detector for receiving the force signal and the position signal, for synchronizing the force signal and the position signal, and for providing an output signal related to the synchronized force signal and position signal; and
    a display for receiving the output signal and for displaying data representing the output signal.

19. An apparatus comprising:
    a hand tool having a sensor for detecting a force exerted by the tool when a user operates the tool and for providing a force signal;
    a position detector coupled to the tool for detecting the position of the tool as the tool is operated, and for providing a position signal;
    a data collector coupled to the tool and to the position detector for receiving the force signal and the position signal, for synchronizing the force signal and the position signal, and for providing an output signal related to the synchronized force signal and position signal; and
    a display for receiving the output signal and for displaying data representing the output signal.

20. The apparatus of claim 19 wherein the position detector detects displacement.

21. The apparatus of claim 19 wherein the position detector is an accelerometer for detecting the rate of the rate of change of the position.

22. An apparatus including an instrumented tool which simulates a working tool used by a worker, the instrumented tool having a sensor for detecting a force exerted by the instrumented tool and for providing a signal indicating the detected force and a cable for carrying the signal, the instrumented tool having about the same weight, weight distribution, size, shape, and feel as the working tool, wherein the instrumented tool includes at least one handle that has approximately the same size, shape and feel as a handle of the working tool.

23. The apparatus of claim 22 wherein the instrumented tool is a driver having a handle and an elongated member having one end coupled to the handle and another end for contacting a workpiece, the driver for rotating the workpiece, the driver having a sensor for detecting a force exerted when the handle is rotated.

24. The apparatus of claim 23 wherein the elongated member extends into an opening in the handle so that a portion of the elongated member can twist relative to the handle, wherein the sensor includes a strain gage coupled to the elongated member at the portion.

25. The apparatus of claim 22 wherein the instrumented tool includes a device having two handles coupled about a fulcrum and a sensor for detecting force exerted when one handle is moved relative to the other.

26. The apparatus of claim 25 wherein the sensor includes a strain gage coupled to one handle near the fulcrum.

27. The apparatus of claim 22 wherein the instrumented tool includes a knife having a blade and a sensor mounted to the blade for detecting a force exerted by the blade in the direction of cutting.

28. The apparatus of claim 27 wherein the blade has a blade edge and oppositely facing sides, the sensor including a strain gage mounted on one side of the knife.

29. The apparatus of claim 22 wherein the tool includes an adapter, the apparatus further comprising a data collector removably and reinsertably coupled to the adapter for receiving the force signal and for providing an output signal which indicates the force exerted by the tool when used, the data collector having a display for receiving the output signal and for displaying information in response to the output signal.

30. An apparatus including:
   an instrumented tool which is a version of a working tool used by a worker, the instrumented tool having:
      a sensor for detecting a force exerted by the instrumented tool and for providing a signal indicating the detected force, and
      a cable for carrying the signal; and
   a data collector having a hand-held housing, the data collector for receiving the signal from the cable.

31. The apparatus of claim 30 wherein the instrumented tool is a version of an actual working tool and having substantially the same size, weight, weight distribution, and feel of the actual working tool.

32. The apparatus of claim 30 wherein the instrumented tool has an adapter electrically coupled to the cable and the data collector has a receptacle, wherein the adapter is removably and reinsertably coupled to the receptacle.

33. The apparatus of claim 32 further including a second tool which is a different type from that of the first tool, the second tool having a sensor for detecting a force exerted by the tool, a cable for providing a signal based at least in part on the force, and an adapter electrically coupled to the cable, the adapter for the second tool being different from the adapter for the first tool and being easily removably and reinsertably coupled to the receptacle.

34. The apparatus of claim 33 wherein the data collector includes means for automatically determining which of the first tool and the second tool is coupled to the receptacle.

35. The apparatus of claim 32 wherein the instrumented tool includes a knife.

36. The apparatus of claim 32 wherein the instrumented tool includes a driver for providing an angular force to a workpiece.

37. The apparatus of claim 32 wherein the instrumented tool includes a device having two handles pivotally coupled about a fulcrum.

38. A method for measuring forces exerted by a hand tool when the hand tool is used, the tool having a sensor which provides an input signal relating to the exerted force during a selected time period, the tool being used for a plurality of repetitions, the method comprising the steps of:
   receiving the force signal when a force is exerted by the tool;
   determining when a repetition occurs during a time period based on a slope or magnitude of the received force signal; and
   providing an output signal indicating a number of repetitions.

39. The method of claim 38 wherein the step of determining comprises the steps of:
   determining a slope for the force signal with respect to time, and
   comparing the slope to a predetermined slope threshold.

40. The method of claim 39 wherein the determining step includes comparing a magnitude of the signal force with a predetermined magnitude threshold.

41. The method of claim 38 further comprising the step of storing the signal in a memory after the receiving step and prior to the determining step.

42. A method for measuring forces exerted by a hand tool when the hand tool is used, the tool having a sensor which provides a force signal relating to the exerted force and a position sensor coupling to one of a user's hand or the tool for providing a position signal indicating a position of one of the user's hand or the tool, the method comprising the steps of:
   receiving the force signal when a force is exerted by the tool;
   receiving a position signal from the position sensor coupled to one of the user's hand or the tool;
   synchronizing the force signal and the position signal; and
   providing an output signal derived from the exerted force and the position.

43. The method of claim 42 wherein the step of receiving a position signal includes receiving a signal from an accelerometer.

44. The method of claim 42 further comprising a step of storing the output signal over time.

45. The method of claim 42 further comprising a step of displaying the output signal on a display.

46. A method for measuring forces exerted by a hand tool when used by a user, the method including the computer implemented steps of:
   receiving from a tool a force signal indicating an exerted force;
   receiving an identification signal from the tool;
   using the identification signal to determine a type of tool that is being used;

accessing data corresponding to the determined type of tool; and providing an output signal derived at least in part from the force signal and from the data corresponding to the determined type of tool.

47. The method of claim 46 further including a step of providing a signal derived from the output signal to a display.

48. The method of claim 47 wherein the output signal includes a signal that causes the display to display a name indicating the determined type of data.

49. The method of claim 46 wherein the step of using the identification signal includes determining the type of tool without additional user input.

50. The method of claim 47 wherein the step of accessing data includes accessing parameters indicating units in which a signal derived from the force signal is displayed.

51. The hand tool measurement kit including:

a plurality of different types of instrumented hand tools, each type of hand tool having a sensor for detecting a force exerted by the tool, and an adapter electrically coupled to the sensor, wherein each and tool is generally similar to a working tool that is used in a workplace; and a data collector for removable and reinsertable coupling to the adapters and for receiving a force signal from the adapter, wherein the measurement kit is usable for testing workers doing normal tasks in the workplace under working conditions.

52. The apparatus as in claim 51 wherein the data collector includes memory for receiving and storing the received force signal.

53. The apparatus of claim 51 wherein the data collector includes memory for storing data corresponding to each different type of tools.

54. An apparatus comprising:

a hand tool having a position sensor for detecting a position of the tool when the tool is used by a user and for providing a position signal that represents the detected position; and a processor, that receives the position signal from the position sensor, and determines when each repetition of the tool occurs based at least in part on a magnitude or slope of the position signal.

* * * * *